(12) United States Patent
Bussmann

(10) Patent No.: US 8,652,092 B2
(45) Date of Patent: Feb. 18, 2014

(54) APPLICATOR

(75) Inventor: Oliver Bussmann, Aschau (DE)

(73) Assignee: Acino AG, Miesbach (DE)

( * ) Notice: Subject to any disclaimer, the term of this patent is extended or adjusted under 35 U.S.C. 154(b) by 265 days.

(21) Appl. No.: 11/921,348

(22) PCT Filed: May 4, 2006

(86) PCT No.: PCT/EP2006/004208
§ 371 (c)(1),
(2), (4) Date: Jul. 13, 2009

(87) PCT Pub. No.: WO2006/128548
PCT Pub. Date: Dec. 7, 2006

(65) Prior Publication Data
US 2009/0299298 A1 Dec. 3, 2009

(30) Foreign Application Priority Data
Jun. 1, 2005 (DE) .......................... 10 2005 025 187

(51) Int. Cl.
*A61M 31/00* (2006.01)
(52) U.S. Cl.
USPC ............................................ 604/59; 604/224
(58) Field of Classification Search
USPC .................... 604/57, 15, 192, 198, 164.08, 59
See application file for complete search history.

(56) References Cited

U.S. PATENT DOCUMENTS

| | | | |
|---|---|---|---|
| 4,474,572 A * | 10/1984 | McNaughton et al. | ......... 604/61 |
| 4,597,753 A | 7/1986 | Turley | |
| 5,338,310 A * | 8/1994 | Lewandowski | ............... 604/192 |
| 6,213,932 B1 | 4/2001 | Schmidt | |
| 6,796,970 B1 | 9/2004 | Klitmose et al. | |
| 2003/0040766 A1 | 2/2003 | Werner | |
| 2006/0258990 A1 | 11/2006 | Weber | |

FOREIGN PATENT DOCUMENTS

| | | | |
|---|---|---|---|
| DE | 621145 | * | 11/1935 |
| DE | 20311996 U1 | | 10/2003 |
| DE | 69818997 T2 | | 9/2004 |
| EP | 1312315 | * | 5/2003 |

* cited by examiner

*Primary Examiner* — Kevin C Sirmons
*Assistant Examiner* — Deanna K Hall
(74) *Attorney, Agent, or Firm* — Edwards Wildman Palmer LLP; Peter F. Corless; Christine C. O'Day

(57) ABSTRACT

The invention relates to applicators (1) for implantation of an implant, having a cylinder (2) and a plunger (3) displaceably mounted therein, which plunger (3) has a pusher plunger (31) for pushing the implant out of a cannula, the cannula being mounted on a cylinder part, the cylinder part (4) being movably guided in the cylinder (2), there being provided a gear mechanism (5) which couples the plunger (3) to the cylinder part (4), a movement of the plunger (3) relative to the cylinder (2) being converted into an opposite movement of the cylinder part (4).

8 Claims, 1 Drawing Sheet

APPLICATOR

Figure 1:
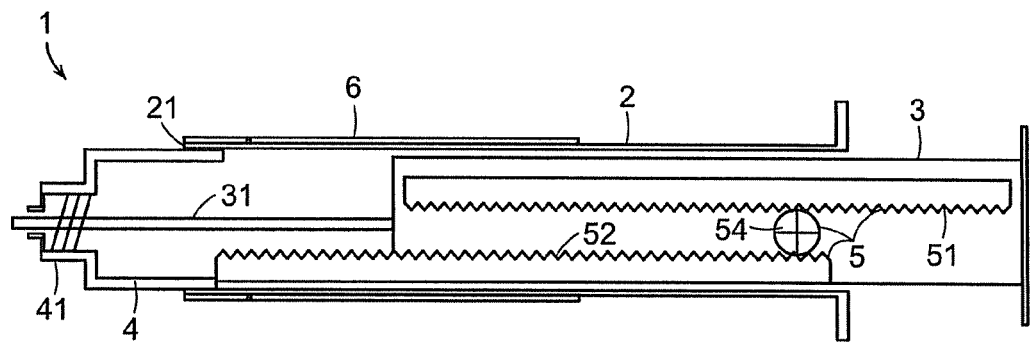

The invention relates to an applicator for implantation of an implant, having a cylinder and a plunger displaceably mounted therein, which plunger has a pusher plunger for pushing the implant out of a cannula.

In the known applicators, implants located in a cannula are, for deposition under the skin or in tissue, introduced under the skin and then pushed out of the cannula by means of a pusher plunger.

For that procedure, the physician must first introduce the cannula of the applicator under the skin and then, by pushing in the plunger and at the same time withdrawing the applicator, make troublefree deposition possible for the implant.

That two-fold movement—exertion of pressure on the pusher plunger by displacement of the plunger with corresponding withdrawal of the entire applicator, including the cannula, from the tissue—which movement has to be co-ordinated exactly, requires skill and practice.

The invention is therefore based on the problem of providing an applicator which allows easier deposition of an implant.

That problem is solved by an applicator having the features of claim 1.

According to the invention, the cannula is mounted or mountable on a cylindrical cannula support or cylinder part, the cylinder part being movably guided in the cylinder, there being provided a gear mechanism which couples the plunger to the cylinder part, a movement of the plunger relative to the cylinder being converted into an opposite movement of the cylinder part.

As a result, controlled by the gear mechanism, the pushing-in of the plunger automatically causes the cannula to be withdrawn in a counter-movement and the implant is thus deposited in a cavity which forms by itself.

In an advantageous and preferred construction in accordance with the invention, the gear mechanism is formed by a first toothed rack joined to or formed on the plunger, which toothed rack is in engagement with a toothed wheel rotatably mounted on a shaft on the cylinder, which toothed wheel is also in engagement with a second toothed rack which is mounted or formed on the cylinder part.

In a modification of the invention that is no less advantageous, the cannula can be formed on the cylinder part or a coupling for mounting such a cannula can be provided.

Accordingly, a development is proposed according to which the coupling is formed by a Luer lock.

Preferably, a sleeve that at least partially surrounds the cylinder is provided, the sleeve being displaceably mounted around the cylinder and being displaceable beyond the coupling-side end of the cylinder until it at least partially surrounds a cannula coupled to the coupling of the applicator.

The sleeve is advantageously guided on the cylinder in a constraining guide means; the constraining guide means can advantageously be formed by a recess in the sleeve and a projection on the outside of the cylinder that engages therein.

Further advantages, special features and advantageous developments of the invention will be found in the further subsidiary claims or combinations thereof with one another.

Figure 2:
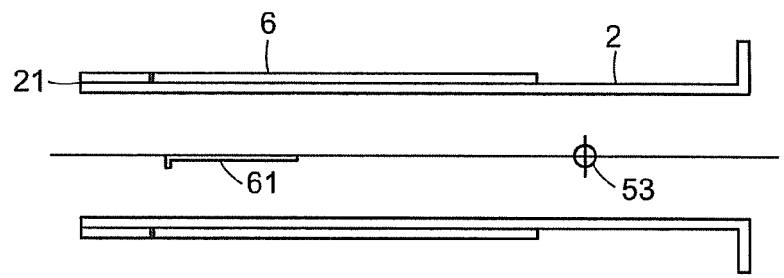
Figure 3:
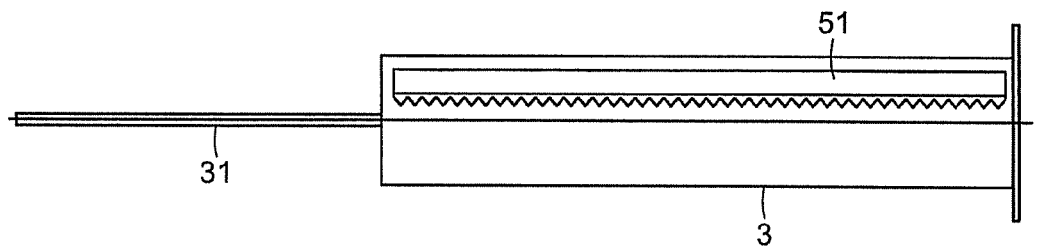
Figure 4:
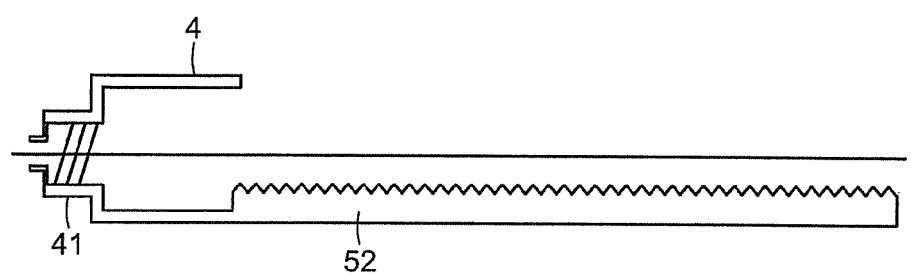

The invention will be described in greater detail below with reference to the drawings, which, in detail, show diagrammatically:

FIG. 1: a diagrammatic sectional view of an applicator according to the invention for implantation of an implant, having a cylinder and a plunger displaceably mounted therein, FIG. 2: a diagrammatic sectional view of the cylinder, having a sleeve guided thereon, without the plunger and the cylinder part, FIG. 3: a diagrammatic sectional view of the plunger, having the toothed rack and pusher plunger formed thereon, and FIG. 4: a diagrammatic sectional view of the cylinder part, having the toothed rack formed thereon and a Luer lock as coupling for a cannula.

Reference numerals that are the same in the Figures denote elements that are the same or have the same action.

FIG. 1 shows a diagrammatic sectional view of an applicator 1 according to the invention for implantation of an implant which for that purpose can be pushed out of a cannula. A cannula having the implant located therein (not shown) is joined to the applicator by means of the coupling 41 which is in the form of a Luer lock.

The applicator 1 has a cylinder 2 which is open at the ends and has a plunger 3 displaceably mounted therein. Formed on the plunger 3 is a pusher plunger 31 which serves for pushing the implant out of a cannula.

The cannula, as already described, is mounted on a cylinder part 4 by means of a coupling 41 which is, for example, in the form of a Luer lock. The cylinder part 4 is in turn movably guided in the cylinder 2.

A gear mechanism 5 couples the plunger 3 to the cylinder part 4 in order to produce a movement of the cylinder part 4 in the opposite direction, and accordingly withdrawal of the cannula mounted on the coupling 41, when the plunger 3 is pushed into the cylinder 2.

The gear mechanism 5 is so configured that it converts a movement of the plunger 3 relative to the cylinder 2 into an opposite movement of the cylinder part 4.

For that purpose, two toothed racks 51 and 52 coupled to a toothed wheel 54 are provided.

A first toothed rack 51 formed on the plunger 3 is in engagement with the toothed wheel 54 rotatably mounted on a shaft 53 on the cylinder 2; see in this connection FIG. 2 and FIG. 3.

The toothed wheel 54 is also in engagement with a second toothed rack 52 which is formed on the cylinder part 4; see also FIG. 4.

Guidance of the plunger 3 and the cylinder part 4 and stabilisation thereof in respect of rotation about the axis is provided by the shaping of the toothed racks 51 and 52 (plate-shaped) together with the toothed wheel 54 rotatably mounted on the shaft 53.

In addition, an end stop can be provided on the cylinder 2 at the front and the rear, which end stop prevents unintentional removal of the plunger 3 from the cylinder 2.

Furthermore, for safeguarding the cannula there is provided a sleeve 6 which at least partially surrounds the cylinder 2, the sleeve 6 being displaceably mounted around the cylinder 2. The sleeve 6 is displaceable beyond the coupling-side end 21 of the cylinder 2 until it is able at least partially to surround a cannula coupled to the coupling 41 of the applicator 1 (see FIG. 1 and FIG. 2).

For that purpose, the sleeve 6 is guided on the cylinder 2 in a constraining guide means, the constraining guide means being formed by a recess in the sleeve 6 and a projection 61 on the outside of the cylinder 2 that engages therein (FIG. 2). Once the physician has installed the implant, for protection against injury he can push the movably mounted sleeve 6 over the cannula and lock it by means of a rotating movement; the constraining guide means can be provided with a right-angled portion for that purpose.

As a result, a device for protection against injury or contamination during handling of the mounted cannula is provided.

All parts of the applicator according to the invention can be produced from a sterilised plastics material.

LIST OF REFERENCE NUMERALS 1 applicator
2 cylinder
21 coupling-side end
3 plunger
31 pusher plunger
4 cylinder part
41 coupling
5 gear mechanism
51 first toothed rack
52 second toothed rack
53 shaft
54 toothed wheel
6 sleeve
61 projection

The invention claimed is:

1. An applicator for implantation of an implant, comprising:
a cylinder and a plunger displaceably mounted therein, which plunger comprises a pusher plunger for pushing the implant out of a cannula,
wherein the cannula is mounted on a cylinder part for movement therewith, the cylinder part being movably guided in the cylinder, there being provided a gear mechanism which couples the plunger to the cylinder part, a movement of the plunger relative to the cylinder being converted into a simultaneous opposite movement of the cylinder part and, thereby, the cannula as the implant is pushed out of the cannula by the pusher plunger.

2. An applicator of claim 1 wherein the gear mechanism comprises a first toothed rack joined to or formed on the plunger, which toothed rack is in engagement with a toothed wheel rotatably mounted on a shaft on the cylinder, which toothed wheel is also in engagement with a second toothed rack which is mounted or formed on the cylinder part.

3. An applicator of claim 1 wherein the cannula is formed on the cylinder part or a coupling for mounting such a cannula is provided.

4. An applicator of claim 3 wherein the coupling comprises a Luer lock.

5. An applicator of claim 1 wherein a sleeve that at least partially surrounds the cylinder is provided, the sleeve being displaceably mounted around the cylinder and being displaceable beyond the coupling-side end of the cylinder until it at least partially surrounds a cannula coupled to the coupling of the applicator.

6. An applicator of claim 5 wherein the sleeve is guided on the cylinder in a constraining guide means, the constraining guide means comprising a recess in the sleeve and a projection on the outside of the cylinder that engages therein.

7. An applicator for implanting an implant, comprising:
a cylinder;
a plunger displaceably mounted in the cylinder, the plunger including a pusher plunger for pushing an implant out of a cannula;
a cylinder part adapted and configured to retain the cannula, the cylinder part being movably guided in the cylinder; and
a gear mechanism mounted in the cylinder for coupling the plunger to the cylinder part,
wherein a movement of the plunger relative to the cylinder is converted into an opposite movement of the cylinder part and, thereby, the cannula as the implant is pushed out of the cannula.

8. An applicator for implantation of an implant by a single movement of a user, the applicator comprising:
a cylinder having an open proximal and distal end;
a cylinder part slidably mounted in the cylinder, the cylinder part having a coupling for securing a cannula near the distal end of the cylinder and a distal toothed cylinder part rack;
a plunger slidably mounted in the cylinder, the plunger having a proximal actuating portion, a toothed plunger rack, and a distal pusher; and
a gear wheel mounted in the cylinder and coupled to the distal toothed cylinder part rack and the toothed plunger rack such that upon sliding the plunger distally, the distal pusher distally urges an implant into a space created by the cannula and, simultaneously, the gear wheel translates a movement of the toothed plunger rack into a proximal movement of the distal toothed cylinder part rack and, thereby, the coupling and a cannula secured thereto are retracted proximally.

* * * * *